United States Patent
Achatz et al.

(10) Patent No.: US 10,604,816 B2
(45) Date of Patent: Mar. 31, 2020

(54) COMBINED SYSTEM FOR PRODUCING STEEL AND METHOD FOR OPERATING THE COMBINED SYSTEM

(71) Applicant: ThyssenKrupp AG, Essen (DE)

(72) Inventors: Reinhold Achatz, Essen (DE); Jens Wagner, Frankfurt a.M. (DE); Markus Oles, Hattingen (DE); Peter Schmöle, Dortmund (DE); Ralph Kleinschmidt, Mülheim a.d.Ruhr (DE); Matthias Patrick Krüger, Herne (DE); Denis Krotov, Dortmund (DE); Olaf von Morstein, Essen (DE)

(73) Assignee: ThyssenKrupp AG, Essen (DE)

( * ) Notice: Subject to any disclaimer, the term of this patent is extended or adjusted under 35 U.S.C. 154(b) by 102 days.

(21) Appl. No.: 15/102,142

(22) PCT Filed: Dec. 11, 2014

(86) PCT No.: PCT/EP2014/003319
§ 371 (c)(1),
(2) Date: Jun. 6, 2016

(87) PCT Pub. No.: WO2015/086153
PCT Pub. Date: Jun. 18, 2015

(65) Prior Publication Data
US 2016/0304978 A1   Oct. 20, 2016

(30) Foreign Application Priority Data
Dec. 12, 2013   (DE) .................... 10 2013 113 921 U

(51) Int. Cl.
*C21C 5/28*     (2006.01)
*C21B 7/00*     (2006.01)
(Continued)

(52) U.S. Cl.
CPC .............. *C21C 5/285* (2013.01); *C01B 3/025* (2013.01); *C01C 1/04* (2013.01); *C07C 29/151* (2013.01);
(Continued)

(58) Field of Classification Search
CPC ...................................................... C21C 5/285
See application file for complete search history.

(56) References Cited

U.S. PATENT DOCUMENTS

2006/0027043 A1   2/2006   Zendejas-Martinez
2009/0249922 A1*  10/2009  Soyland .............. C21B 13/0073
                                                              75/505
(Continued)

FOREIGN PATENT DOCUMENTS

CN           1311825 A       9/2001
DE     202011105262 U1      10/2012
(Continued)

OTHER PUBLICATIONS

PCT Application No. PCT/EP2014/003319, International Search Report and Written Opinion, dated Jun. 18, 2015, 17 pages.
(Continued)

*Primary Examiner* — Scott R Kastler
(74) *Attorney, Agent, or Firm* — Lathrop GPM LLP

(57) ABSTRACT

The invention relates to a plant complex for steel production comprising a blast furnace for producing pig iron, a converter steel mill for producing crude steel and a gas-conducting system for gases that occur in the production of pig iron and/or in the production of crude steel. According to the invention, the plant complex additionally has a chemical or biotechnological plant connected to the gas-conducting system and a plant for producing hydrogen. The plant for producing hydrogen is connected to the gas-conducting
(Continued)

system by a hydrogen-carrying line. Also the subject of the invention is a method for operating the plant complex.

4 Claims, 2 Drawing Sheets

(51) Int. Cl.

| | | |
|---|---|---|
| C25B 15/08 | (2006.01) | |
| C25B 1/04 | (2006.01) | |
| C21B 5/06 | (2006.01) | |
| C21C 5/38 | (2006.01) | |
| C01B 3/02 | (2006.01) | |
| C01C 1/04 | (2006.01) | |
| C07C 29/151 | (2006.01) | |
| C12M 1/00 | (2006.01) | |
| C21B 3/04 | (2006.01) | |
| C21B 5/00 | (2006.01) | |
| C21C 1/00 | (2006.01) | |
| C21C 5/40 | (2006.01) | |
| F01L 15/10 | (2006.01) | |
| F01K 7/30 | (2006.01) | |

(52) U.S. Cl.
CPC .............. *C12M 43/00* (2013.01); *C21B 3/04* (2013.01); *C21B 5/00* (2013.01); *C21B 5/06* (2013.01); *C21B 7/002* (2013.01); *C21C 1/00* (2013.01); *C21C 5/38* (2013.01); *C21C 5/40* (2013.01); *C25B 1/04* (2013.01); *C25B 15/08* (2013.01); *F01K 7/30* (2013.01); *F01L 15/10* (2013.01); *C21B 2100/60* (2017.05); *C21B 2100/62* (2017.05); *C21C 2100/02* (2013.01); *C21C 2100/04* (2013.01); *C21C 2100/06* (2013.01); *Y02E 60/366* (2013.01); *Y02P 10/143* (2015.11); *Y02P 10/283* (2015.11); *Y02P 20/133* (2015.11)

(56) References Cited

U.S. PATENT DOCUMENTS

| | | |
|---|---|---|
| 2010/0064855 A1 | 3/2010 | Lanyi et al. |
| 2012/0226080 A1 | 9/2012 | Meyer-Pittroff |
| 2014/0343339 A1 * | 11/2014 | Schodel .................. C07C 41/01 585/639 |
| 2016/0304978 A1 | 10/2016 | Achatz et al. |

FOREIGN PATENT DOCUMENTS

| | | |
|---|---|---|
| DE | 102011077819 A1 | 12/2012 |
| DE | 102013113913 A1 | 6/2015 |
| DE | 102013113921 A1 | 6/2015 |
| DE | 102013113942 A1 | 6/2015 |
| DE | 102013113950 A1 | 6/2015 |
| DE | 102013113958 A1 | 6/2015 |
| DE | 102013113980 A1 | 6/2015 |
| EP | 200880 A2 | 11/1986 |
| EP | 244551 A1 | 3/1990 |
| EP | 2543743 A1 | 1/2013 |
| EP | 2657215 A1 | 10/2013 |
| EP | 3080308 A1 | 10/2016 |
| FR | 2420568 A1 | 10/1979 |
| JP | 61275101 A | 12/1986 |
| JP | 2004309067 A | 11/2004 |
| JP | 2011225969 A | 11/2011 |
| RU | 2125613 C1 | 1/1999 |
| WO | 0005421 A1 | 2/2000 |
| WO | 2010136313 A1 | 12/2010 |
| WO | 2011018124 A1 | 2/2011 |
| WO | WO-2011116141 A2 * | 9/2011 ............. B82Y 30/00 |
| WO | 2015086148 A1 | 6/2015 |
| WO | 2015086149 A1 | 6/2015 |
| WO | 2015086150 A1 | 6/2015 |
| WO | 2015086151 A1 | 6/2015 |
| WO | 2015086152 A1 | 6/2015 |
| WO | 2015086153 A1 | 6/2015 |
| WO | 2015086154 A1 | 6/2015 |

OTHER PUBLICATIONS

PCT Application No. PCT/EP2014/003319, International Preliminary Report on Patentability dated Jun. 14, 2016, 8 pages.
Zhang Q et al, Recovery and Utilization of By-Product Gases in Iron and Steel Works, vol. 44, No. 12, China Academic Journal Electronic Publishing House, www/cnki.net, dated Dec. 2009, 5 pages.
Canadian Application No. 2,930,470, Office Action dated Mar. 6, 2017, 5 pages.
Roshina S.I. et al. Operation, Repair and Maintenance of Buildings and Structures, Textbook, Vladimir, Publishing House VIGU, 2005, 108 pages.
Australian Application No. 2014361208, Examination Report dated Apr. 9, 2018, 10 pages.
Schmole et al., Ecological Hot Metal Production Using Coke Plant and Blast Furnace Route, La Revue de Metallurgie-CIT, Mar. 1, 2005, pp. 171-182, Bd. 102, Nr. 3, 1, XP001230940, Paris, FR.
EP Application No. 14815581.5 Office Action dated Aug. 28, 2018.
Ghanbari et al, Optimal Design and Operation of a Steel Plant Integrated With a Polygeneration System.

* cited by examiner

COMBINED SYSTEM FOR PRODUCING STEEL AND METHOD FOR OPERATING THE COMBINED SYSTEM

CROSS-REFERENCE TO RELATED APPLICATIONS

This application is the national phase of, and claims priority to, International Patent Application No. PCT/EP2014/003319, filed Dec. 11, 2014, which designated the U.S. and which claims priority to German Patent Application Number DE 10 2013 113 921.3, filed Dec. 12, 2013. These applications are each incorporated by reference herein in their entireties.

BACKGROUND

1. Field of the Invention

The invention relates to a plant complex for steel production and to a method for operating the plant complex.

2. Description of the Related Art

Pig iron is obtained in blast furnaces from iron ores, additives and also coke and other reducing agents such as coal, oil, gas, biomasses, recycled waste plastics or other substances containing carbon and/or hydrogen. CO, $CO_2$, hydrogen and water vapour inevitably occur as products of the reduction reactions. In addition to the aforementioned constituents, a blast-furnace top gas drawn off from the blast-furnace process often has a high content of nitrogen. The amount of gas and the composition of the blast-furnace top gas are dependent on the feedstock and the operating mode and are subject to fluctuations. Typically, however, blast-furnace top gas contains 35 to 60% by volume $N_2$, 20 to 30% by volume CO, 20 to 30% by volume $CO_2$ and 2 to 15% by volume $H_2$. Around 30 to 40% of the blast-furnace top gas produced in the production of the pig iron is generally used for heating up the hot air for the blast-furnace process in air heaters; the remaining amount of top gas may be used externally in other areas of the works for heating purposes or for electricity generation.

In the converter steel mill, which is arranged downstream of the blast-furnace process, pig iron is converted into crude steel. By blowing oxygen onto liquid pig iron, troublesome impurities such as carbon, silicon, sulphur and phosphorus are removed. Since the oxidation processes cause an intense development of heat, scrap is often added in amounts of up to 25% with respect to the pig iron as a coolant. Furthermore, lime is added for forming slag and an alloying agent. A converter gas that has a high content of CO and also contains nitrogen, hydrogen and $CO_2$ is drawn off from the steel converter. A typical converter gas composition has 50 to 70% by volume CO, 10 to 20% by volume $N_2$, about 15% by volume $CO_2$ and about 2% by volume $H_2$. The converter gas is either burned off or, in the case of modern steel works, captured and passed on to be used for providing energy.

The plant complex may optionally be operated in combination with a coking plant. In this case, the plant complex described at the beginning additionally comprises a coke-oven plant, in which coal is converted into coke by a coking process. In the coking of coal into coke, a coke-oven gas occurs, containing a high hydrogen content and considerable amounts of $CH_4$. Typically, coke-oven gas contains 55 to 70% by volume $H_2$, 20 to 30% by volume $CH_4$, 5 to 10% by volume $N_2$ and 5 to 10% by volume CO. In addition, the coke-oven gas has fractions of $CO_2$, $NH_3$ and $H_2S$. In practice, the coke-oven gas is used in various areas of the works for heating purposes and in the power-generating process for electricity generation. In addition, it is known to use coke-oven gas together with blast-furnace top gas or with converter gas for producing syngases. According to a method known from WO 2010/136313 A1, coke-oven gas is separated into a hydrogen-rich gas stream and a residual gas stream containing $CH_4$ and CO, the residual gas stream being fed to the blast-furnace process and the hydrogen-rich gas stream being mixed with blast-furnace top gas and processed further into a syngas. It is known from EP 0 200 880 A2 to mix converter gas and coke-oven gas and use them as a syngas for methanol synthesis.

In an integrated metallurgical plant that is operated in combination with a coking plant, approximately 40 to 50% of the raw gases that occur as blast-furnace top gas, converter gas and coke-oven gas are used for chemical engineering processes. Approximately 50 to 60% of the gases produced are fed to the power-generating plant and used for electricity generation. The electricity produced in the power-generating plant covers the electricity demand for the production of pig iron and crude steel. Ideally, the energy balance is closed, so that, apart from iron ores and carbon in the form of coal and coke as sources of energy, no further energy input is necessary and, apart from crude steel and slag, no product leaves the plant complex.

SUMMARY OF THE INVENTION

It is an object of the invention to further improve the cost-effectiveness of the overall process and provide a plant complex with which it is possible to reduce the costs for steel production.

DETAILED DESCRIPTION

Figure 1:
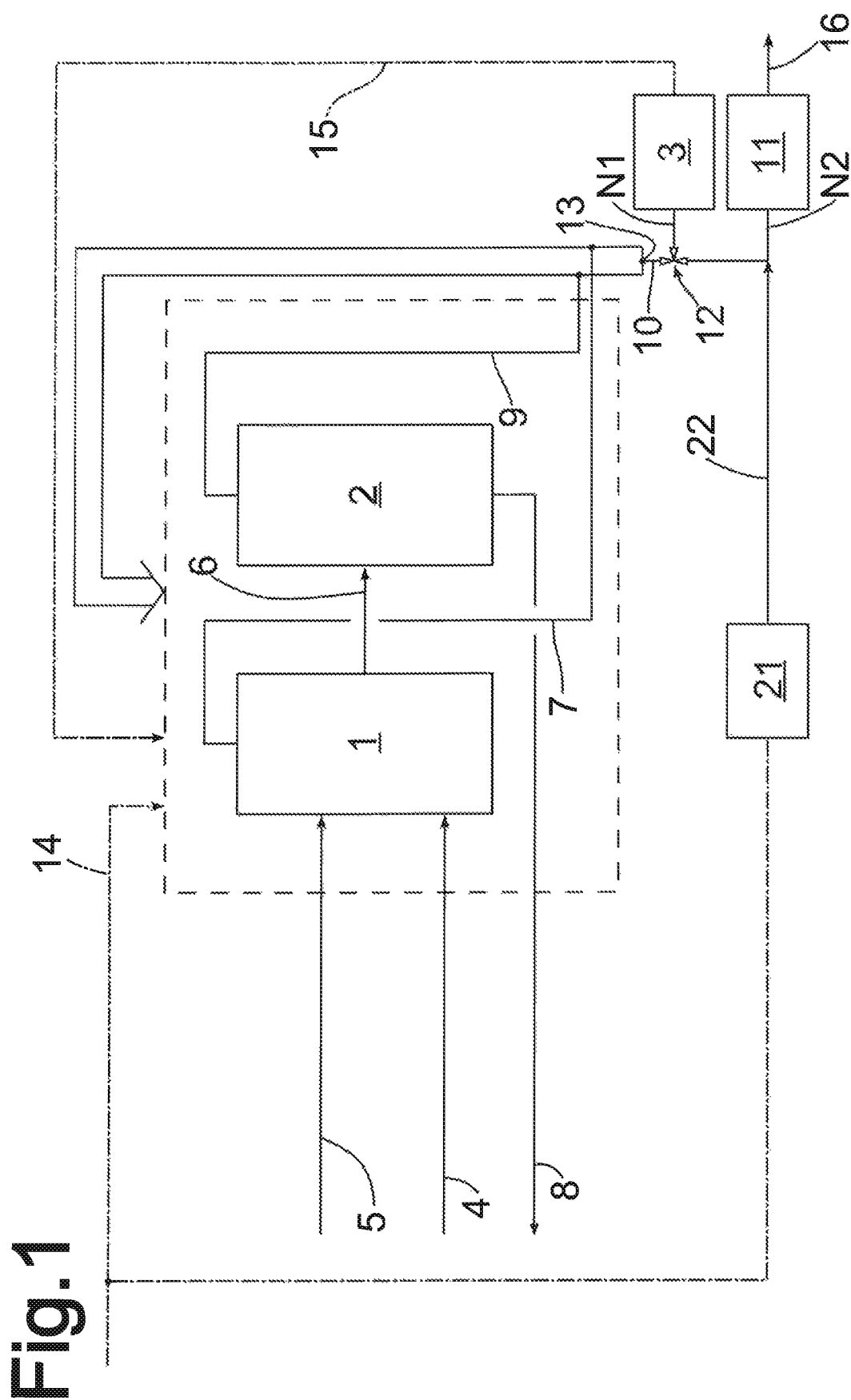
FIG. 1 is a simplified block diagram of a plant complex for producing steel comprising a blast furnace for producing pig iron, a converter steel works for producing crude steel, a power-generating plant, a chemical or biotechnological plant and a plant for producing hydrogen.

In one embodiment, a plant complex for steel production comprises at least one blast furnace for producing pig iron, a converter steel mill for producing crude steel, and a gas-conducting system for gases that occur in the production of pig iron and/or in the production of crude steel. The plant complex may also have a power-generating plant for electricity generation, which is designed as a gas-turbine power-generating plant or gas-turbine and steam-turbine power-generating plant and is operated with a gas that comprises at least a partial amount of the blast-furnace top gas that occurs in the production of pig iron in the blast furnace and/or a partial amount of the converter gas that occurs in the converter steel mill.

Proceeding from a plant complex for producing steel comprising a blast furnace for producing pig iron, a converter steel mill for producing crude steel and a gas-conducting system for gases that occur in the production of pig iron and/or in the production of crude steel, according to the invention a chemical or biotechnological plant connected to the gas-conducting system and a plant for producing hydrogen are provided, wherein the plant for producing hydrogen is connected to the gas-conducting system by a hydrogen-carrying line.

Also the subject of the invention is a method for operating a plant complex for producing steel that has at least one blast furnace for producing pig iron, a converter steel mill, a chemical plant or biotechnological plant and a plant for producing hydrogen. According to one embodiment of the method, at least a partial amount of a blast-furnace top gas that occurs in the production of pig iron in the blast furnace and/or a partial amount of a converter gas that occurs in the production of crude steel is used after a gas-conditioning operation as a useful gas for producing chemical products in a chemical plant or biotechnological plant. The useful gas here, prior to being used as syngas, is enriched with hydrogen that is formed in the plant for producing hydrogen. Converter gas or blast-furnace top gas, or a mixed gas formed from blast-furnace top gas and converter gas, can generate syngases which consist essentially of CO and $H_2$ of which the composition is coordinated with a subsequent process in the chemical plant or the biotechnological plant. A specific addition of hydrogen that is produced within the plant complex makes it possible for the ratio of CO and hydrogen to be adjusted very precisely and varied over a wide parameter range.

In the chemical plant, chemical products can be produced from syngases that respectively contain the components of the end product. Chemical products may be for example ammonia or methanol or else other hydrocarbon compounds.

For producing ammonia, a syngas that contains nitrogen and hydrogen in the correct ratio must be provided. The nitrogen can be obtained from blast-furnace top gas. Blast-furnace top gas or converter gas may be used as the hydrogen source, hydrogen being produced by conversion of the CO fraction by a water-gas-shift reaction ($CO+H_2O \rightleftharpoons CO_2+H_2$). For producing hydrocarbon compounds, for example methanol, it is necessary to provide a syngas consisting substantially of CO and/or $CO_2$ and $H_2$ that contains the components carbon monoxide and/or carbon dioxide and hydrogen in the correct ratio. The ratio is often described by the module $(H_2-CO_2)/(CO+CO_2)$. The hydrogen may be produced for example by conversion of the CO fraction in the blast-furnace top gas by a water-gas-shift reaction. Converter gas may be used for providing CO. Blast-furnace top gas and/or converter gas may serve as a source of $CO_2$.

In the case of the concepts described above, however, it is not possible for the C content or N content of the mixed gas to be used in full since there is a shortage of hydrogen. In order for it to be possible for the C content or N content of the gases that occur during the production of pig iron and/or the production of crude steel to be used in full for producing chemical products, the invention introduces hydrogen that is formed in a plant for producing hydrogen. The hydrogen is produced preferably by electrolysis of water, wherein the electrolysis of water is operated expediently by electric power which has been produced from renewable energy. The electrolysis of water also produces oxygen that can be used in the blast furnace for producing pig iron and/or in the converter steel works for producing crude steel.

It is also within the scope of the invention for syngas to be produced from converter gas and enriched with hydrogen. The enrichment with hydrogen that is produced within the plant complex, in accordance with the hydrogen requirement, makes it possible to adjust the $H_2$ content of the converter gas to any desired value.

It is also possible to use blast-furnace top gas and converter gas to produce a mixed gas which, after a gas-conditioning operation and enrichment with hydrogen, is used as syngas for producing chemical products. It is expedient here for the hydrogen to be produced by electrolysis of water using electricity obtained from renewable energy.

Within the scope of the invention, a biotechnological plant may also be used instead of a chemical plant for producing products from syngas. The plant concerned is a plant for the fermentation of syngas. The syngas is used biochemically by way of a fermentation process, it being possible to produce products such as alcohols (ethanol, butanol), acetone or organic acids. These products, which are produced by fermentation of syngas, are also only mentioned by way of example in the present case.

According to a preferred embodiment of the invention, the plant complex additionally comprises a coke-oven plant. If the production of pig iron and the production of crude steel are operated in combination with a coking plant, a partial amount of the blast-furnace top gas that occurs in the production of pig iron and/or a partial amount of the converter gas that occurs in the converter steel mill may be mixed with a partial amount of the coke-oven gas that occurs in the coke-oven plant and the mixed gas may be used as a useful gas. A mixture of coke-oven gas and blast-furnace top gas or a mixed gas comprising coke-oven gas, converter gas and blast-furnace top gas may be used as a useful gas for producing a syngas, for example for ammonia synthesis. A mixed gas comprising coke-oven gas and converter gas or a mixed gas comprising coke-oven gas, converter gas and blast-furnace top gas is suitable for producing hydrocarbon compounds. The described chemical products that can be produced in a chemical plant from blast-furnace top gas, converter gas and coke-oven gas are only application examples for explaining the variants of the method that are described in the patent claims.

The raw gases—coke-oven gas, converter gas and blast-furnace top gas—may be conditioned individually or in combinations as a mixed gas and then fed to the chemical plant as syngases. The conditioning of coke-oven gas in particular comprises a cleaning of the gas to separate out troublesome contents, in particular tar, sulphur and sulphur compounds, aromatic hydrocarbons (BTX) and high-boiling hydrocarbons. A gas-conditioning operation is also necessary for producing the syngas. In the course of the gas conditioning, the proportion of the components CO, $CO_2$ and $H_2$ within the raw gas is changed. The gas conditioning comprises for example pressure swing adsorption for separating out and enriching $H_2$ and/or a water-gas-shift reaction for converting CO into hydrogen and/or a steam reformer for converting the $CH_4$ fraction into CO and hydrogen in the coke-oven gas.

According to a preferred embodiment of the invention, the plant complex comprises a power-generating plant for electricity generation which is designed as a gas-turbine power-generating plant or gas-turbine/steam-turbine power-generating plant that is operated with a gas that comprises at least a partial amount of the blast-furnace top gas that occurs in the production of pig iron in the blast furnace and/or a partial amount of the converter gas that occurs in the converter steel works. The power-generating plant for electricity generation and the chemical plant or biotechnological plant are connected in parallel, as seen in relation to the flow guidance of the gases. The steams of gas that are fed to the power-generating plant, on the one hand, and to the chemical or biotechnological plant, on the other hand, can be controlled.

In the case of the method according to the invention, at least a partial amount of the blast-furnace top gas that occurs in the production of pig iron in the blast furnace and/or a partial amount of the converter gas that occurs in the converter steel works is used as raw gas, in order to produce products, that is to say substances of value, from them by chemical reactions in a chemical plant or by biochemical processes in a biotechnological plant. As a consequence of using part of these gases, the plant complex has a deficit of electricity, which has to be obtained externally. The externally obtained electricity may originate from conventional power-generating plants or be obtained from renewable energy sources. Preferably, the externally obtained electricity is obtained completely or at least partially from renewable energy and originates for example from wind turbine generator plants, solar plants, geothermal power-generating plants, hydroelectric power-generating plants, tidal power-generating plants and the like. To achieve operation of the plant complex that is as cost-effective as possible, at times of low electricity prices electricity is bought in and used for supplying to the plant complex and the part of the useful gas that is not used for producing electricity is used for producing chemical products after a gas-conditioning operation in the chemical plant or the biotechnological plant. At times of high electricity prices, on the other hand, the useful gas is completely or at least mostly fed to the power-generating plant in order to produce electricity for supplying to the plant complex. The chemical plant or biotechnological plant is correspondingly operated at a lower output at times of high electricity prices. The same applies for the electrolysis of water operated with electric power. If, in the event of high electricity prices, the chemical plant is operated at a lower output, it is also the case that the level of hydrogen required is low. If, in contrast, in the event of electricity prices being low, the chemical plant is operated with a high production output, it is also possible for the hydrogen to be produced cost-effectively by electrolysis of water. A closed-loop control system is provided for operating the method, establishing the alternating operation of the power-generating plant on the one hand and the chemical plant or biotechnological plant on the other hand in dependence on a variable process parameter. The process parameter is preferably determined in dependence on a function that includes the price for the externally obtained electricity and the costs for producing the power-generating plant electricity as variables.

The method according to the invention makes it possible for the plant complex to be operated cost-effectively. The method according to the invention thereby also makes use in particular of the fact that the efficiency of a power-generating process for producing electricity is worse than the efficiency of a chemical plant or a biotechnological plant in which chemical products are produced by chemical reactions or by biochemical processes from syngas.

The product output of the chemical plant or of the biotechnological plant is controlled in dependence on the amount of syngas fed to this plant. A major challenge for the chemical plant is that of finding a way of operating dynamically with changing plant loads. The way of operating with changing plant loads can be realized in particular by the chemical plant having a plurality of small units arranged in parallel, which are individually switched on or off depending on the available stream of useful gas.

The use of a biotechnological plant has the advantage that a biotechnological plant is more flexible with respect to load changes than a chemical plant.

The invention also covers the use of a chemical or biotechnological plant for coupling to a metallurgical plant.

Referring now to the figures, the plant complex for steel production that is represented in FIG. 1 comprises a blast furnace 1 for producing pig iron, a converter steel mill 2 for producing crude steel, a power-generating plant 3 for electricity generation and a chemical or biotechnological plant 11.

In the blast furnace 1, pig iron 6 is obtained substantially from iron ore 4 and reducing agents 5, in particular coke and coal. Reduction reactions cause the production of a blast-furnace top gas 7, which contains nitrogen, CO, $CO_2$ and $H_2$ as the main constituents. In the converter steel mill 2 that is arranged downstream of the blast-furnace process, pig iron 6 is converted into crude steel 8. By blowing oxygen onto the liquid pig iron, troublesome impurities, in particular carbon, silicon and phosphorus, are removed. For cooling, scrap may be added in amounts of up to 25% with respect to the amount of pig iron. Furthermore, lime is added for forming slag and an alloying agent. At the top of the converter, a converter gas 9 that has a very high proportion of CO is drawn off.

The power-generating plant 3 is designed as a gas-turbine power-generating plant or gas-turbine and steam-turbine power-generating plant and is operated with a gas that comprises at least a partial amount of the blast-furnace top gas 7 that occurs in the production of pig iron in the blast furnace 1 and/or a partial amount of the converter gas 9 that occurs in the converter steel works 2. A gas-conducting system is provided for carrying the gases.

According to the overall balance represented in FIG. 1, carbon is fed to the plant complex as a reducing agent 5 in the form of coal and coke and also iron ore 4. Occurring as products are crude steel 8 and raw gases 7, 9, which differ in amount, composition, calorific value and purity and are used again at various points in the plant complex. In an overall consideration, 40 to 50%, usually approximately 45%, of the raw gases 7, 9 are returned again into the metallurgical process for producing pig iron or producing crude steel. Between 50 and 60%, usually approximately 55%, of the raw gases 7, 9 can be used for operating the power-generating plant 3. The power-generating plant 3 operated with a mixed gas 10 comprising blast-furnace top gas 7 and converter gas 9 is designed in such a way that it can cover the electricity demand of the plant complex.

According to the representation in FIG. 1, a chemical or biotechnological plant 11 is provided, connected to the gas-conducting system and arranged in parallel with the power-generating plant 3 with respect to the gas supply. The gas-conducting system has an operationally controllable gas diverter 12 for dividing the streams of gas that are fed to the power-generating plant 3 and the chemical or biotechnological plant 11. Provided upstream of the gas diverter in the direction of flow is a mixing device 13, for producing the mixed gas 10 consisting of blast-furnace top gas 7 and converter gas 9.

In the case of the plant complex represented in FIG. 1, at least a partial amount of the blast-furnace top gas 7 that occurs in the production of pig iron in the blast furnace 1 and a partial amount of the converter gas 9 that occurs in the production of crude steel are used as a useful gas for operating the power-generating plant 3 and the chemical or biotechnological plant 11. Externally obtained electricity 14 and power-generating plant electricity 15, which is produced by the power-generating plant 3 of the plant complex, are used to cover the electricity demand of the plant complex. The proportion of electricity accounted for by the externally obtained electricity 14 with respect to the overall electricity demand of the plant complex is established as a variable process parameter and the amount of useful gas N1 fed to the power-generating plant 3 is determined in dependence on this process parameter. The part of the useful gas N2 that is not used for producing electricity is used after a gas-conditioning operation as a syngas for producing chemical products 16 or is fed after a gas-conditioning operation to the biotechnological plant and used for biochemical processes.

The externally obtained electricity 14 is preferably obtained completely or at least partially from renewable energy and originates for example from wind turbine generator plants, solar plants, hydroelectric power-generating plants and the like. The process parameter on the basis of which the amount of useful gas N1 that is fed to the power-generating process is established is determined in dependence on a function that includes the price for the externally obtained electricity and the costs for producing the power-generating plant electricity 15 as variables. To achieve operation of the plant complex that is as cost-effective as possible, at times of low electricity prices electric power is bought in as external electricity 14 and used for supplying electricity to the plant complex, the part of the useful gas N2 that is not used for producing electricity being fed to the chemical or biotechnological plant 11 and used for producing chemical products 16 after a gas-conditioning operation. At times of high electricity prices, the raw gases 7, 9 that occur in the production of pig iron and the production of crude steel are fed to the power-generating plant 3 in order to produce electricity for supplying to the plant complex. The chemical plant 11 or the alternatively provided biotechnological plant is correspondingly operated at a lower output at times of high electricity prices.

In order that the carbon content and the nitrogen content of the raw gases that occur during operation of the plant complex can be used in full for producing chemical products, hydrogen has to be fed in order to compensate for a shortage of hydrogen. The plant complex therefore additionally has a plant 21 for producing hydrogen, which is connected to the gas-conducting system by a hydrogen-carrying line 22. The plant 21 for producing hydrogen may be in particular an electrolysis plant for the electrolysis of water. Electrolysis of water is energy-intensive to operate and is therefore primarily put into operation at times of low electricity prices, at which the chemical plant 11 or biotechnological plant is also operated and the power-generating plant 3 is operated at a lower output. The hydrogen that is additionally produced is fed to the chemical plant 11 together with the useful gas as syngas. This allows the capacity of the chemical plant 11 to be increased significantly. The same applies correspondingly if a biotechnological plant is provided instead of the chemical plant 11.

Figure 2:
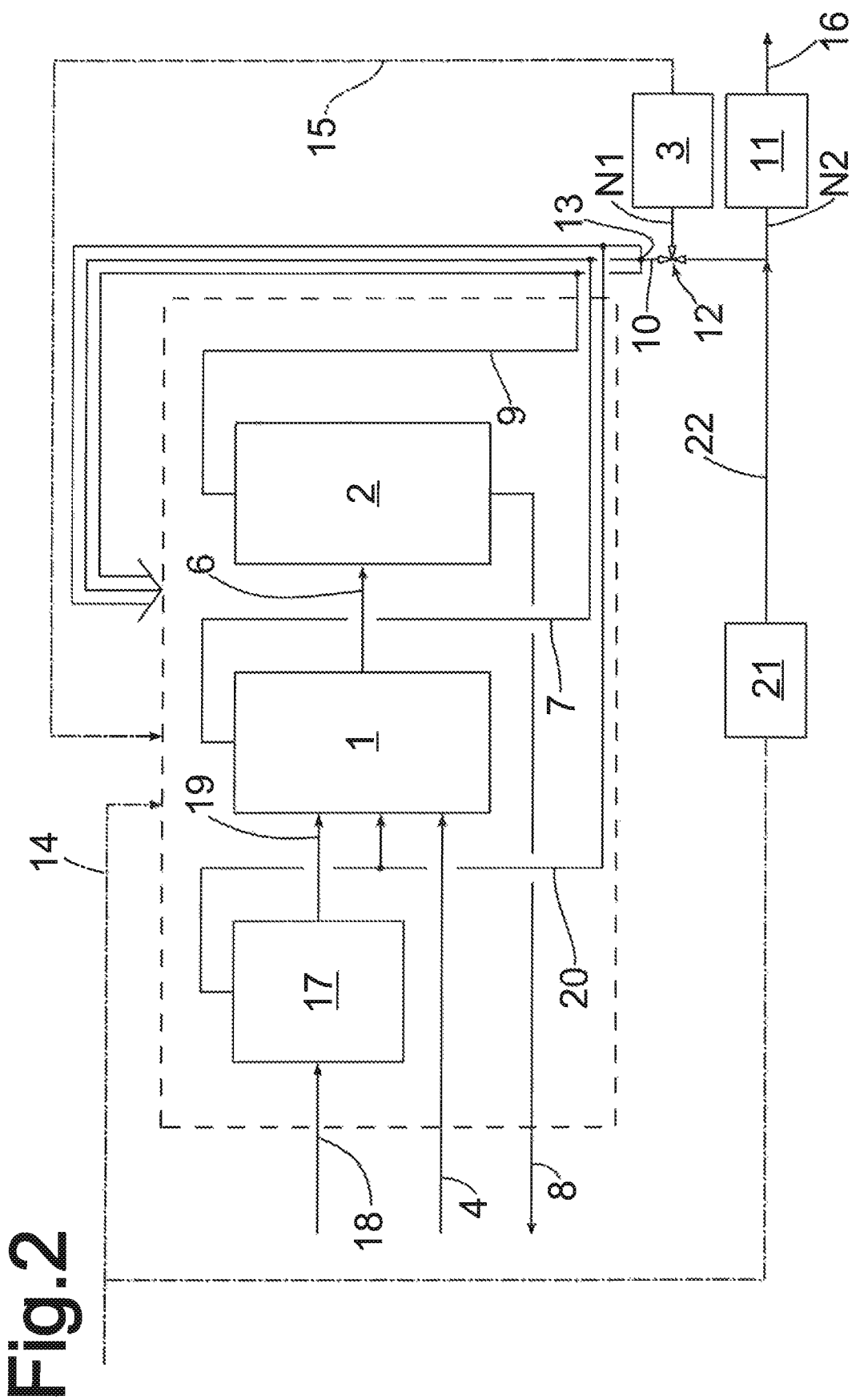
FIG. 2 is a simplified block diagram of a plant complex which, in addition to a blast furnace for producing pig iron, a converter steel works for producing crude steel, a power-generating plant, a chemical or biotechnological plant and a plant for producing hydrogen, also comprises a coke-oven plant.

In the exemplary embodiment of FIG. 2, the plant complex additionally comprises a coke-oven plant 17. In the coking of coal 18 into coke 19, coke-oven gas 20 occurs, containing a high proportion of hydrogen and $CH_4$. Parts of the coke-oven gas 20 may be used for the heating of the air heaters in the blast furnace 1. The gas-conducting system includes a gas distribution for the coke-oven gas 20. Provided upstream of the gas diverter 12 in the direction of flow is a mixing device 13, for producing a mixed gas 10 consisting of blast-furnace top gas 7, converter gas 9 and coke-oven gas 20. With the gas diverter 12, the streams of gas that are fed to the power-generating plant 3 and the chemical or biotechnological plant 11 can be controlled.

During the operation of the plant represented in FIG. 2, a partial amount of the blast-furnace top gas 7 that occurs in the production of pig iron and/or a partial amount of the converter gas 9 that occurs in the converter steel works are mixed with a partial amount of the coke-oven gas 20 that occurs in the coke-oven plant 17. The mixed gas 10 is used for operating the power-generating plant 3 and, after a gas-conditioning operation and enrichment with hydrogen, as syngas in the chemical plant 11 or biotechnological plant.

The blast-furnace top gas 7, the converter gas 9 and the coke-oven gas 20 may be combined with one another in any way desired. The combination of gas streams 7, 9, 20 depends on the desired syngas or the product that is to be produced from the syngas in the chemical plant 11 or the biotechnological plant. An additional enrichment with hydrogen, which is produced preferably by water electrolysis in the plant 21, takes place here.

Many different arrangements of the described invention are possible without departing from the spirit and scope of the present invention. Embodiments of the present invention are described herein with the intent to be illustrative rather than restrictive. Alternative embodiments will become apparent to those skilled in the art that do not depart from its scope. A skilled artisan may develop alternative means of implementing the disclosed improvements without departing from the scope of the present invention.

Further, it will be understood that certain features and subcombinations are of utility and may be employed without reference to other features and subcombinations and are contemplated within the scope of the claims. Not all steps listed in the various figures and description need to be carried out in the specific order described. The description should not be restricted to the specific described embodiments.

The invention claimed is:
1. A plant complex for steel production comprising
a blast furnace for producing pig iron;
a converter steel mill for producing crude steel;
a chemical plant or a biotechnological plant;
a hydrogen-producing plant;
a power-generating plant;
a gas-conducting system for gases that occur in the production of pig iron and/or the production of crude steel; and
a closed-loop control system;
wherein:
the chemical plant or biotechnological plant is connected to the gas-conducting system and the hydrogen-producing plant;
the hydrogen-producing plant is connected to the gas-conducting system via a hydrogen-carrying line and has an electrolysis plant for the electrolysis of water;
the power-generating plant is designed as a gas-turbine and steam-turbine power-generating plant and is operated with a gas comprising blast furnace top gas occurring in the production of pig iron in the blast furnace and converter gas that occurs in the converter steel mill;
the chemical plant or biotechnological plant is arranged in parallel with the power-generating plant with respect to the gas supply;
the gas-conducting system comprises a connectable gas diverter operably connected to the closed-loop control system for selectively altering a ratio of the streams of gas that are fed to the power-generating plant and the chemical plant or biotechnological plant, wherein:
  at a first electricity price, a portion of the streams of gas is diverted from the power-generating plant to the chemical plant or biotechnological plant;
  at a second electricity price, a portion of the streams of gas is diverted from the chemical plant or biotechnological plant to the power-generating plant; and
  the second electricity price is greater than the first electricity price; and
  the hydrogen-carrying line is connected to a mixing device and is arranged upstream of the chemical or biotechnological plant relative to the direction of flow, and wherein at least one of the blast furnace top gas and the converter gas is enriched with hydrogen prior to entering the mixing device.

2. The plant complex according to claim 1, wherein the chemical plant or biotechnological plant is connected to a line for converter gas, and wherein the hydrogen-carrying line is connected to the converter-gas line, so that the converter gas, for use in the chemical plant or biotechnological plant, is enriched with hydrogen.

3. The plant complex according to claim 1, wherein the electrolysis plant is connected to at least one of the blast furnace and to a plant for producing crude steel by means of an oxygen-return device.

4. A plant complex, comprising:
  a biotechnological plant for fermentation of a syngas and an electrolysis plant for producing hydrogen by the electrolysis of water coupled to a metallurgical plant, the metallurgical plant comprising:
    at least one blast furnace for producing pig iron; and
    a converter steel mill;
  a power generating plant comprising one of:
    a gas-turbine power-generating plant; and
    a gas-turbine and steam-turbine power-generating plant; and
  a closed-loop control system;
  wherein:
    the biotechnological plant is arranged in parallel with the power-generating plant with respect to the gas supply;
    a partial amount of at least one of blast furnace top gas that occurs in the production of pig iron and converter gas that occurs in the converter steel mill is fed to the chemical or biotechnological plant, and after a gas-conditioning operation and enrichment with hydrogen, is used as syngas for producing chemical products;
    at least a partial amount of blast furnace top gas from the production of pig iron and converter gas from the converter steel mill is fed to the power-generating plant; and
    a gas conducting system comprises a gas diverter operably connected to the closed-loop control system for dividing the streams of gas fed to the power-generating plant and the chemical or biotechnological plant.

* * * * *